(12) United States Patent
Hunger et al.

(10) Patent No.: US 10,302,622 B2
(45) Date of Patent: May 28, 2019

(54) WOOD TEST TOOL AND METHOD FOR VISUALLY CHECKING A WOOD OBJECT

(71) Applicant: IML Instrumenta Mechanik Labor GmbH, Wiesloch (DE)

(72) Inventors: Erich Hunger, Karlsruhe (DE); Sebastian Hunger, Wiesloch (DE); Fabian Hunger, Leimen (DE)

(73) Assignee: IML Instrumenta Mechanik Labor GmbH, Wiesloch (DE)

( * ) Notice: Subject to any disclaimer, the term of this patent is extended or adjusted under 35 U.S.C. 154(b) by 100 days.

(21) Appl. No.: 15/320,761

(22) PCT Filed: Jun. 11, 2015

(86) PCT No.: PCT/EP2015/001173
§ 371 (c)(1),
(2) Date: Dec. 21, 2016

(87) PCT Pub. No.: WO2016/058650
PCT Pub. Date: Apr. 21, 2016

(65) Prior Publication Data
US 2017/0212095 A1    Jul. 27, 2017

(30) Foreign Application Priority Data
Oct. 15, 2014  (DE) .................. 10 2014 015 051

(51) Int. Cl.
*G01N 33/46* (2006.01)
*B26F 1/38* (2006.01)
*G01N 1/08* (2006.01)

(52) U.S. Cl.
CPC ........... *G01N 33/46* (2013.01); *B26F 1/3846* (2013.01); *G01N 1/08* (2013.01)

(58) Field of Classification Search
CPC .... G01N 33/46; G01N 1/08; G01N 2001/085; B26F 1/3846
(Continued)

(56) References Cited

U.S. PATENT DOCUMENTS 2,688,877 A * 9/1954 Peine ................... G01N 1/08
73/864.64
2,968,184 A * 1/1961 Archer ................. G01N 1/08
73/863.81
(Continued)

FOREIGN PATENT DOCUMENTS

DE  4200426 * 7/1993
WO  84/01827  5/1984

OTHER PUBLICATIONS

Forster T et al.: "Increment Puncher: A tool for extracting small cores of wood and bark from living trees"; IAWA Journal, vol. 21 (2), 2000: 169-180.
(Continued)

*Primary Examiner* — Robert R Raevis
(74) *Attorney, Agent, or Firm* — Gudrun E. Huckett

(57) ABSTRACT

The present invention relates to a wood test tool (1) for punching out and visually checking the core of a wood sample. The wood test tool (1) has a hollow cylindrical pin (11), comprising at one end an input opening (12) which corresponds to the inner diameter of the hollow cylinder, and at the other end a flattened head (13) as well as a viewing window (14), said viewing window extending over at least two thirds along the length of the hollow cylinder starting from the end of the hollow cylindrical pin (11) on the side of the input opening. Further disclosed is a method for checking the impregnation depth of an impregnated wood object (4).

20 Claims, 3 Drawing Sheets

(58) Field of Classification Search
USPC ........ 73/864.44, 864.45, 865.8, 866; 83/515,
83/518, 667, 669, 670, 681, 682,
83/684–691, 698.71; 175/20, 58, 236
See application file for complete search history.

(56) References Cited

U.S. PATENT DOCUMENTS

| | | | | |
|---|---|---|---|---|
| 2,987,922 | A | * | 6/1961 | Harrington ............... G01N 1/08 73/864.44 |
| 4,117,896 | A | * | 10/1978 | Weber ..................... E21B 12/06 175/308 |
| 4,595,321 | A | | 6/1986 | Van Dalen |
| 4,738,142 | A | * | 4/1988 | Morgan .................... G01N 1/08 374/157 |
| 5,501,283 | A | * | 3/1996 | Nordquist ................ A01B 1/24 172/22 |
| 6,015,248 | A | * | 1/2000 | Elliott ................... B23B 31/117 408/204 |
| 6,102,135 | A | * | 8/2000 | Shaw ..................... E21B 11/005 175/20 |

OTHER PUBLICATIONS

Anonymous: "BGS Locheinsatz,565, 9-tlg. in Kunststoffkassette, 3-12 mm" Amazon.de: Baumarkt; Apr. 25, 2007; XP055216610; see international search report.

Kottlors C et al: "Probenahme aus Holz und Holzwerkstoffen zur Klärung von Fragen des Holzschutzes durch chemische Untersuchungen"; Holz Als Roh- Und Werkstoff; Springer-Verlag, Berlin, Germany; vol. 51, No. 2, pp. 126-134; Aug. 3, 2013; see international search report.

Furniss M M: "A circular punch for cutting samples of bark infested with beetles"; Canadian Entomologist; Ottawa, Canada; vol. 94, No. 9, pp. 959-963; Sep. 1962; XP008177618; see international search report.

* cited by examiner

WOOD TEST TOOL AND METHOD FOR VISUALLY CHECKING A WOOD OBJECT

BACKGROUND OF THE INVENTION

The invention relates to a wood testing tool for punching out and visually inspecting a wood sample core. In addition, the invention relates to a method for inspecting the impregnation depth of an impregnated wooden object.

Trees, but also wooden masts and other wooden objects exposed to weathering, have to be inspected from time to time to see whether their stability can still be guaranteed or whether there is rot, etc., inside the wooden object. For this purpose, drill resistance measurements are taken, wherein inferences as to the state of the wood can be drawn from the drilling resistance measured. If the wood objects to be checked are impregnated, this has an influence on the drill resistance measurement. It is therefore important to known in advance how deep an impregnation goes, so that corresponding adjustments can be made when evaluating the measurement results, for example.

Hence, the determination of the impregnation depth in addition to the drilling resistance measurement is an important parameter when it comes to assessing masts for rot. Problems with rot frequently occur in masts due to poor impregnation. With the help of the impregnation depth, incipient rot and existing cavities which are identified by the drilling resistance measurement can be evaluated more effectively and more meaningfully.

Starting from this state of the art, the problem addressed by the present invention is that of creating a tool with which the impregnation depth of a wooden object can easily be demonstrated.

SUMMARY OF THE INVENTION

This problem is solved by a wood testing tool characterized in that the wood testing tool has a hollow cylindrical pin which has at one end a driving-in opening corresponding to the internal diameter of the hollow cylinder and, at the other end, a flattened head and an inspection window which, starting from the end of the hollow cylindrical pin at the driving-in opening end, extends over at least two-thirds of the length of the hollow cylinder. The problem is further solved by the wood testing set comprising a wood testing tool according to the invention, an ejector, and a guide sleeve, wherein the guide sleeve has a bore that widens at one end into a receiving section for the tip of the wood testing tool with the driving-in opening, and wherein the wood testing tool with the driving-in opening at the tip can be received in the receiving section of the guide sleeve and the ejector can be introduced from the other end of the guide sleeve through the bore in a centered manner into the hollow cylindrical pin.

Developments are set out in the dependent claims.

A method enables the impregnation depth of a wooden object to be inspected quickly and easily, wherein the method comprises driving-in of the wood testing tool with the driving-in opening into the wooden object, wherein a wood sample core is received in the hollow cylindrical pin up to a penetration depth that is greater than a presumed impregnation depth; removal of the wood testing tool from the wooden object; visual inspection of the wood sample core through the inspection window of the wood testing tool, said core exhibiting at least one section stained by impregnation and an unstained section, and determining of the impregnation depth with the help of a length of the stained section.

A wood testing tool according to the invention is used for punching outs and visually inspecting a core of a wood sample, in order to check the impregnation depth of an impregnated wooden object. For this purpose, the wood testing tool has a hollow cylindrical pin comprising at one end a driving-in opening corresponding to the internal diameter of the hollow cylinder and, at the other end, a flattened head. Furthermore, the hollow cylindrical pin has an inspection window in the form of a longitudinal recess which, starting from the end of the hollow cylindrical pin at the driving-in opening end, extends over at least two-thirds of the length of the hollow cylinder and therefore allows a visual check of the wood sample core contained in the wood cylinder to be made quickly and easily after punching out.

The inspection window may extend as far as the head, if necessary, so that the wood testing tool can be driven as far as possible into the wooden object to be tested and the length of the wood sample core that can be inspected can therefore be maximized. The width of the inspection window in this case is designed so that the wood sample core can easily be recognized and, at the same time, the wood tool is guaranteed to be sufficiently stable to be driven into the wooden object. It is therefore provided that the width of the inspection window accounts for no more than a quarter, preferably roughly an eighth, or less, of the outer periphery of the hollow cylindrical pin.

For a particularly simple and quick evaluation of the penetration depth of the hollow cylindrical pin in the wooden object to be tested and of the impregnation depth, in a further embodiment of the tool according to the invention, a scale can be provided on the outer surface of the hollow cylindrical pin in the longitudinal direction, for example adjacent to the inspection window or, alternatively, circumferentially, which scale extends at least along the length of the inspection window. In this case, the driving-in opening forms a reference point of the scale, irrespective of whether the scale extends as far as the driving-in opening or not, so that the penetration depth of the wood testing tool is correlated with the scale.

So that the wood testing tool can be well driven into the wooden object to be tested, the end with the driving-in opening may be tapered and/or exhibit cutting edge. The expenditure of force required to drive it in can thereby be reduced.

In order to exhibit the stability necessary for driving in and permanent durability, the wood testing tool may be made of metal, preferably steel, or another material which is sufficiently hard—possibly a plastic with high strength, impact resistance, rigidity and hardness, such as a polycarbonate or polyphenylene sulfide, for example, are also conceivable.

In order to fix the wood sample core within the wood testing tool, so that the wood sample core is held together and the scale can be read correctly, the wood testing tool may exhibit an elastically compressible cylinder plug which is arranged in the hollow cylindrical pin at the head end. Particularly in a tool with a continuous bore, the cylinder stopper prevents pieces of the sample core from being able to escape from the opening at the head when the tool is being driven in. The diameter of the cylinder plug corresponds to the internal diameter of the hollow cylinder and its length corresponds to at least half the length of the hollow cylinder. The cylinder plug is preferably made of a cellular substance;

however, other elastically deformable materials, such as rubber, for example, or resilient structures, are also conceivable.

In order to make the wood testing tool easier to remove from the wooden object after it has been driven in, the head may exhibit a greater diameter than the pin, so that the head can be drawn out of the wooden object by a corresponding tool equivalent to a nail puller. The head in this case may preferably be of cone-shaped configuration, as a result of which a projection of the head when driving in is easier to achieve, making it easier to grip with the nail puller.

A method according to the invention for inspecting the impregnation depth of an impregnated wooden object uses a wood testing tool according to the invention and involves the driving-in of the wood testing tool with the driving-in opening into the wooden object, wherein a wood sample core is received in the hollow cylindrical pin. Known values for the impregnation depth exist for each of the wooden objects, said values usually lying in the region of 2 to 4 cm, but possibly also, in the case of pine wood, for example, lying around 8 to 10 cm. The chosen depth by which the pin is driven into the wooden object is therefore correspondingly greater, for example more than 5 cm or between 5 and 10 cm, but also above 10 cm. Once the wood testing tool has been pulled out of the wooden object again, the visual inspection of the wood sample core takes place through the inspection window of the wood testing tool, said core exhibiting at least one section stained by impregnation and an unstained section. Using the length of the stained section, which can preferably be read by means of the scale on the wood testing tool, the impregnation depth can be determined.

In addition, it is advantageous for a wood testing set to be used to remove the wood sample core and, to this extent, to inspect a plurality of cores in succession, said wood testing set comprising the wood testing tool according to the invention, an ejector and a guide sleeve. Said guide sleeve has a bore that is configured to receive the matching hollow cylinder so that it fits and that widens at one end into a receiving section for the tip of the wood testing tool with the driving opening, so that the wood testing tool with the driving-in opening at the tip can be received in the receiving section of the guide sleeve. The ejector is then introduced from the other end of the guide sleeve through the bore in a centered manner into the hollow cylindrical pin and therefore has corresponding dimensions which match the hollow cylinder. By applying a small amount of pressure to the ejector to push it, the wood sample core can be removed and the tool is available to take the next sample.

Further embodiments and also some of the advantages associated with these and further embodiments are made clear and more comprehensible by the following detailed description making reference to the accompanying figures. Objects or parts thereof which are substantially identical or similar may be provided with the same reference numbers. The figures are only a schematic representation of an embodiment of the invention.

DESCRIPTION OF PREFERRED EMBODIMENTS

Figure 1:
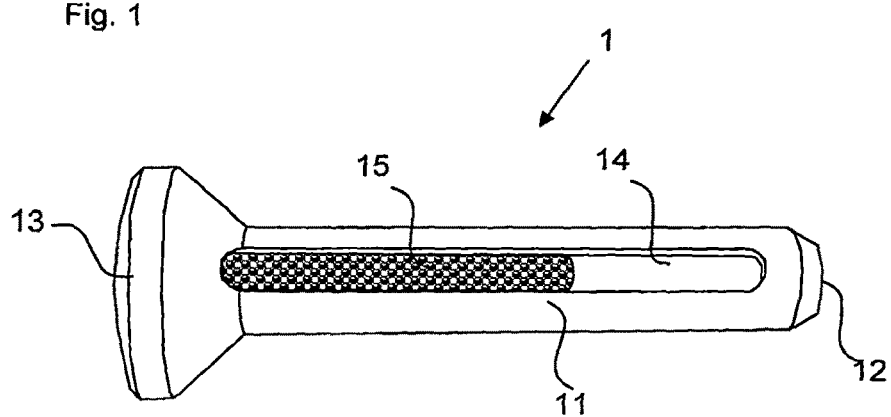
FIG. 1 shows a perspective view of a wood testing tool according to the invention.

Using the wood testing tool 1 according to the invention, which is depicted in FIG. 1, the impregnation depth of impregnated wooden objects, e.g. wooden masts, can be inspected.

Figure 5:
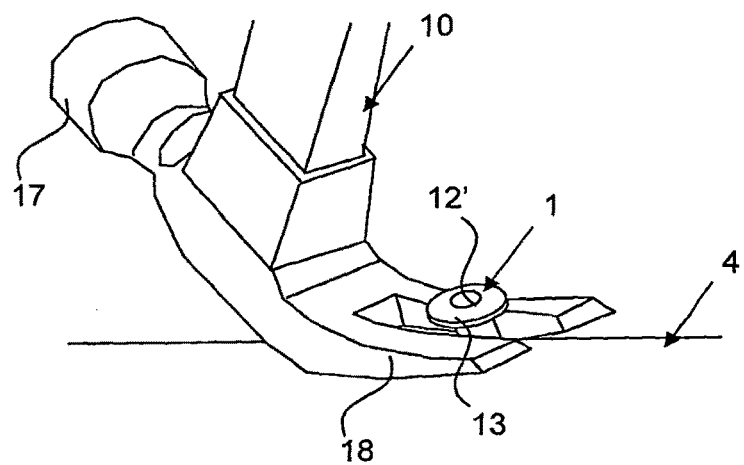
FIG. 5 shows a perspective view of an actuating tool during the pulling-out from a wooden object of a wood testing tool according to the invention.

The wood testing tool 1 comprises a hollow cylindrical pin 11 which has an insertion opening 12 at one end that corresponds to the internal diameter of the hollow cylinder. At the other end, the hollow cylindrical pin 11 has a flattened head 13. If necessary, the bore through the pin 11 may also be continuous, so that there may also be an opening 12' at the head 13, as shown in FIG. 5. The hollow cylindrical pin 11 of a wood testing tool 1 according to the invention may, for example, exhibit a length of 10 cm, so that penetration depths of up to roughly 8 cm can easily be realized, and penetration depths of up to 7 cm can therefore be clearly identified. The internal diameter of the hollow cylindrical pin 11 may then measure 4 to 5 mm, for example. These values should only be seen as exemplary, however; deviations therefrom fall within the scope of protection of the invention.

Figure 2:
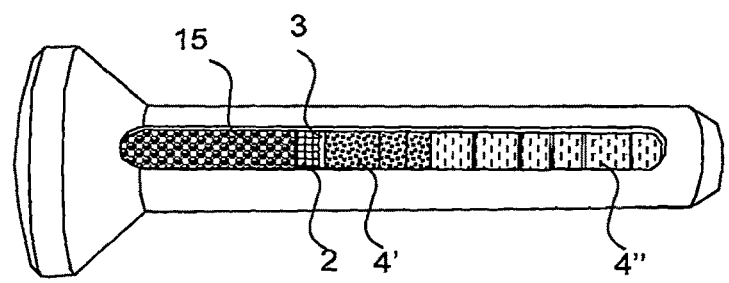
FIG. 2 shows a perspective view of a wood testing tool according to the invention with a sample core.

The elastically compressible cylinder plug 15 arranged in the hollow cylindrical pin 11, which is preferably made of a cellular material, then not only fixes the wood sample core in the pin 11, but also closes the second opening 12' and thereby prevents the sample core from being able to emerge from it. The inspection window 14 in the hollow cylindrical pin 11 allows the wood sample core to be assessed immediately after it has been punched out, without it having to be removed from the wood testing tool 1, as shown in FIG. 2. It is thereby ensured that the core remains intact.

The cylinder plug 15 made of cellular material is compressed during the punching-out of the wood sample core which exhibits stained sections 4' due to impregnation and unstained, non-impregnated sections 4", as a result of which the wood sample core is held inside the pin 11, even if it is dry and fragile. Hence, the penetration depth can easily be determined, particularly when a scale is arranged alongside the inspection window 14 (e.g. printed on or laser-etched). A scale with circumferential notches 19 which mark the distance from the tool tip with the driving-in opening 12 is drawn in FIG. 6. With a scale of this kind, the penetration depth of the wood testing tool 1 can be checked when it is driven into a wooden object.

The length of the cylinder plug 15 is arbitrary, as long as it satisfies the requirements of holding the wood sample core in the pin. The cylinder plug 15 may preferably have a length corresponding to the pin 11, so that it is in abutment when the wood testing tool 1 bears against the wooden object and is then compressed by the penetrating wood sample core when the wood testing tool 1 is driven into the wooden object. If the wood testing tool 1 has a head opening 12', as depicted in FIG. 5, the cylinder plug 15 may also be pushed out slightly from the head opening 12' by the penetrating wood sample core, depending on the length during the driving-in of the wood testing tool 1 into the wooden object. However, this does not have a disadvantageous effect; the wood sample core is still held in the hollow cylinder, so that the impregnation depth can be assessed with the help of a cohesive sample core.

Figure 3A:
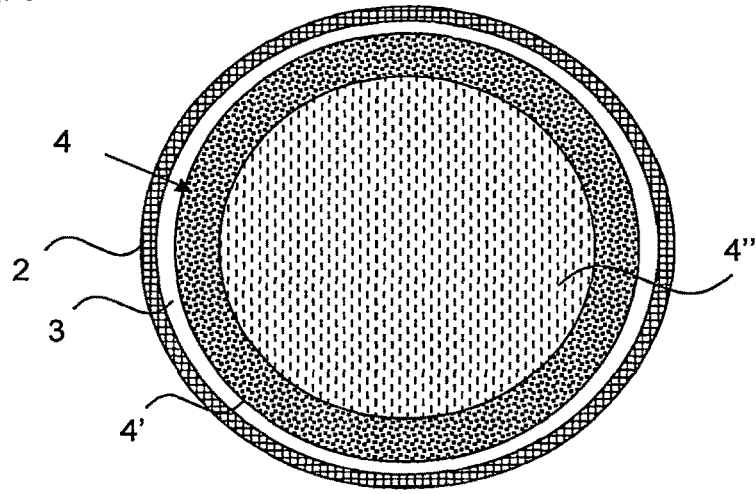
FIG. 3 shows a) a cross-sectional view through a wooden mast protected by a metal-reinforced film and b) a corresponding plug.

FIG. 3a shows a mast 4 protected from mechanical and biological damage by a two-layer film of metal 3 and plastic 2 with an impregnated section 4' and a non-impregnated section 4" as the wooden object to be tested.

Figure 3B:
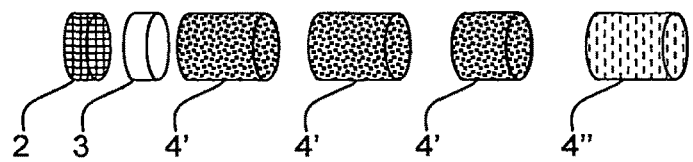

FIG. 3b illustrates what the wood sample cores looks like in this case: in addition to the impregnated sections 4' and the non-impregnated section 4" which differs in color from the impregnated sections 4', the sample core then also comprises a punched-out metal and film piece 3, 2. A corresponding sample core can also be seen in FIG. 2 in the wood testing tool 1 through the inspection window 14. The wood sample core is represented in a plurality of sections owing to the fact that a wood sample core of this kind may, in reality, disintegrate into sections.

Figure 4A:
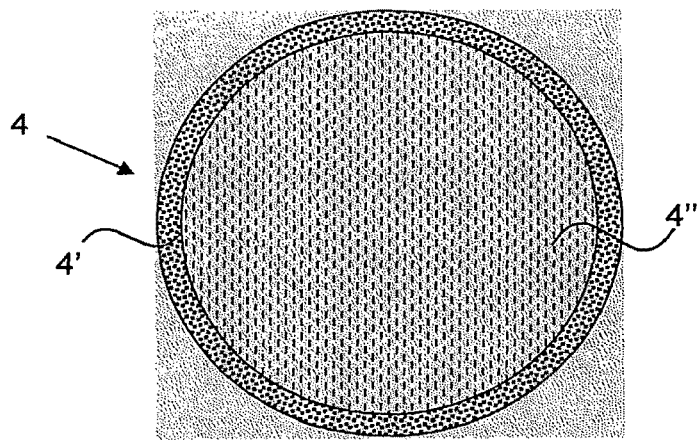
FIG. 4 shows a) a cross-sectional view through a wooden mast with a smaller penetration depth and b) a corresponding plug.
Figure 4B:
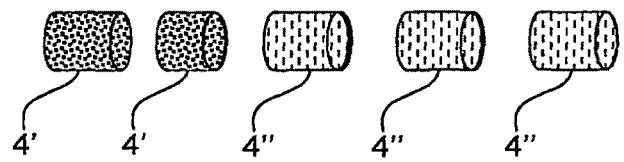

FIG. 4a shows an unprotected wooden mast in which the impregnated section 4' has a smaller depth than that in FIG. 3a. This is also shown in the wood sample core depicted in FIG. 4b with the impregnated sections 4' and the non-impregnated sections 4".

So that samples from wooden objects 4 which are protected by a film-wrapped metal layer (e.g. brass), as with the wooden mast in FIG. 3a, can be taken using the wood testing tool 1 according to the invention, said tool is made of hardened steel. For softer woods, wood testing tools 1 made of different steel or metal alloys, possibly also plastic, can also be used where necessary.

Penetration of the wooden object is supported in that the end of the hollow cylindrical pin 11 on the driving-in opening side is pointed or tapered. Alternatively or in addition, the driving-in opening may be configured with a cutting edge.

The head 13 usually has a greater diameter than the pin 11, so that it can be removed from the wooden object 4 more easily, as can be seen in FIG. 5. The tool 10 used for this purpose is similar to a carpenter's hammer which has a trough-shaped part with a wedge slot, the so-called nail lifter 18, and a hammer head 17 which has advantageously been used beforehand to drive the wood testing tool 1 into the wooden object.

Figure 6:
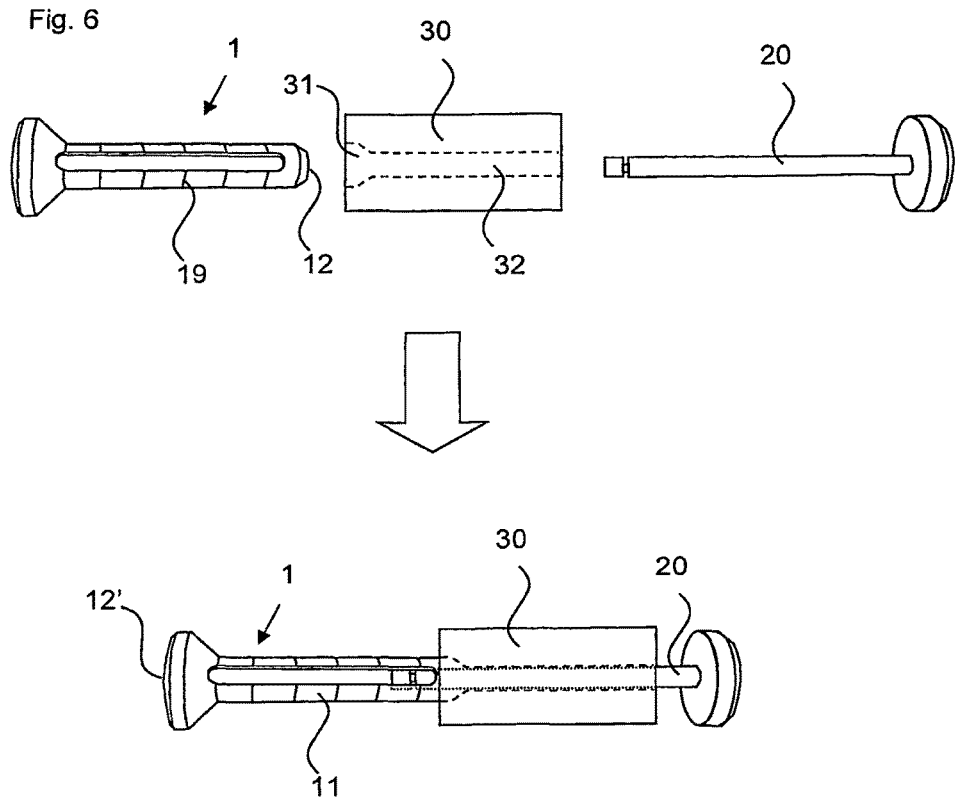
FIG. 6 shows a perspective side view of a wood testing tool with a set for removing the sample core.

In order to be able to remove the sample core from the hollow cylindrical pin 11 in a simple and defined manner, an ejector set, as shown by way of example in FIG. 6, can be used, which comprises an ejector 20 and a guide sleeve 30. The guide sleeve 30 has a bore 32 which expands at one end to a receiving section 31 for the tip of the wood testing tool 1 with the drive-in opening 12. In order to eject the sample core, the wood testing tool 1 with the drive-in opening 12 at the tip is placed in the receiving section 31 of the guide sleeve 30 and the ejector 20 is introduced from the other end of the guide sleeve 30 through the bore 32 in a centered manner into the hollow cylindrical pin 11, in order to eject the sample core that is present there from the head opening 12'.

The invention claimed is:

1. A wood testing tool for punching out and visually inspecting a wood sample core, the wood testing tool comprising:
    a pin comprising a hollow cylinder body and comprising a first end and a second end opposite the first end;
    the first end comprising a driving-in opening having a diameter corresponding to an internal diameter of the hollow cylinder body;
    the second end comprising a flattened head;
    the pin comprising an inspection window that extends from the first end over at least two-thirds of a length of the pin toward the second end and has a width that amounts to not more than a quarter of an outer periphery of the hollow cylinder body;
    wherein the pin comprises an outer surface and the outer surface comprises a scale extending in a longitudinal direction of the pin, wherein the scale is positioned adjacent to the inspection window or extends circumferentially about the pin, wherein the scale extends at least along a length of the inspection window and wherein the driving-in opening is a reference point of the scale.

2. The wood testing tool as claimed in claim 1, wherein the inspection window extends as far as the flattened head.

3. The wood testing tool as claimed in claim 1, wherein the width of the inspection window amounts to not more than one eighth of the outer periphery of the hollow cylinder body.

4. The wood testing tool as claimed in claim 1, wherein the inspection window extends as far as the flattened head and wherein the width of the inspection window amounts to not more than one eighth of the outer periphery of the hollow cylinder body.

5. The wood testing tool as claimed in claim 1, wherein the first end with the driving-in opening is tapered.

6. The wood testing tool as claimed in claim 1, wherein the first end with the driving-in opening has a cutting edge.

7. The wood testing tool as claimed in claim 1, wherein the first end with the driving-in opening is tapered and has a cutting edge.

8. The wood testing tool as claimed in claim 1, wherein the wood testing tool is made of metal.

9. The wood testing tool as claimed in claim 8, wherein the metal is steel.

10. The wood testing tool as claimed in claim 1, wherein the flattened head has a greater diameter than the hollow cylinder body.

11. The wood testing tool as claimed in claim 10, wherein the flattened head has a cone-shaped configuration.

12. A method for inspecting an impregnation depth of an impregnated wooden object using a wood testing tool as claimed in claim 1, the method comprising:
    driving the wood testing tool with the driving-in opening leading into the wooden object, wherein a wood sample core is received in the hollow cylinder body of the pin up to a penetration depth that is greater than a presumed impregnation depth;
    removing the wood testing tool from the wooden object;
    visually inspecting the wood sample core through the inspection window of the wood testing tool, wherein the wood sample core comprises at least one section stained by impregnation and an unstained section;
    determining the impregnation depth based on a length of the stained section.

13. A wood testing tool for punching out and visually inspecting a wood sample core, the wood testing tool comprising:
    a pin comprising a hollow cylinder body and comprising a first end and a second end opposite the first end;
    the first end comprising a driving-in opening having a diameter corresponding to an internal diameter of the hollow cylinder body;
    the second end comprising a flattened head;

the pin comprising an inspection window that extends from the first end over at least two-thirds of a length of the pin toward the second end and has a width that amounts to not more than a quarter of an outer periphery of the hollow cylinder body;

wherein the wood testing tool comprises an elastically compressible cylinder plug arranged inside the hollow cylinder body at the second end, wherein the cylinder plug has a diameter corresponding to the internal diameter of the hollow cylinder body, wherein the cylinder plug has a length that amounts to at least half the length of the hollow cylinder body.

14. A method for inspecting an impregnation depth of an impregnated wooden object using a wood testing tool as claimed in claim 13, the method comprising:

driving the wood testing tool with the driving-in opening leading into the wooden object, wherein a wood sample core is received in the hollow cylinder body of the pin up to a penetration depth that is greater than a presumed impregnation depth;

removing the wood testing tool from the wooden object;

visually inspecting the wood sample core through the inspection window of the wood testing tool, wherein the wood sample core comprises at least one section stained by impregnation and an unstained section;

determining the impregnation depth based on a length of the stained section.

15. The wood testing tool as claimed in claim 13, wherein the inspection window extends as far as the flattened head and wherein the width of the inspection window amounts to not more than one eighth of the outer periphery of the hollow cylinder body.

16. The wood testing tool as claimed in claim 13, wherein the first end with the driving-in opening is tapered and has a cutting edge.

17. The wood testing tool as claimed in claim 13, wherein the wood testing tool is made of metal.

18. A wood testing set comprising:

a wood testing tool comprising a pin comprising a hollow cylinder body and comprising a first end and a second end opposite the first end, wherein the first end comprises a driving-in opening having a diameter corresponding to an internal diameter of the hollow cylinder body and the second end comprises a flattened head, wherein the pin comprises an inspection window that extends from the first end over at least two-thirds of a length of the pin toward the second end and has a width that amounts to not more than a quarter of an outer periphery of the hollow cylinder body;

an ejector;

a guide sleeve comprising a first end and a second end, wherein the guide sleeve comprises a bore that widens at the first end of the guide sleeve into a receiving section for the first end of the wood testing tool comprising the driving-in opening;

wherein the wood testing tool is configured to be received with the first end thereof comprising the driving-in opening in the receiving section of the guide sleeve;

wherein the ejector is configured to be introduced from the second end of the guide sleeve through the bore in a centered manner into the hollow cylinder body of the pin.

19. A method for inspecting an impregnation depth of an impregnated wooden object using a wood testing tool set as claimed in claim 18, the method comprising:

driving the wood testing tool with the driving-in opening leading into the wooden object, wherein a wood sample core is received in the hollow cylindrical body of the pin up to a penetration depth that is greater than a presumed impregnation depth;

removing the wood testing tool from the wooden object;

visually inspecting the wood sample core through the inspection window of the wood testing tool, wherein the wood sample core exhibits at least one section stained by impregnation and an unstained section;

determining the impregnation depth as a length of the stained section.

20. The method as claimed in claim 19, further comprising:

introducing the wood testing tool with the driving-in opening into the receiving section of the guide sleeve;

introducing the ejector from the second end of the guide sleeve through the bore in a centered manner into the hollow cylinder body;

applying pressure to the ejector and ejecting the wood sample core from a head opening of the flattened head of the wood testing tool.

* * * * *